United States Patent
Schröder et al.

(10) Patent No.: US 7,176,309 B2
(45) Date of Patent: Feb. 13, 2007

(54) METHOD FOR PRODUCING MELEM-FREE MELAMINE AND QUENCHING AGENTS

(75) Inventors: Frank Schröder, Albrechtshain (DE); Wolfgang Ruech, Taiskirchen (AT); Christoph Neumüller, Linz (AT); Ferdinand Koglgruber, Linz (AT); Hans Christian Wagner, Vienna (AT)

(73) Assignee: AMI - Agrolinz Melamine International GmbH, Linz (AT)

( * ) Notice: Subject to any disclaimer, the term of this patent is extended or adjusted under 35 U.S.C. 154(b) by 0 days.

(21) Appl. No.: 10/495,619

(22) PCT Filed: Nov. 14, 2002

(86) PCT No.: PCT/DE02/04251

§ 371 (c)(1), (2), (4) Date: Nov. 4, 2004

(87) PCT Pub. No.: WO03/045927

PCT Pub. Date: Jun. 5, 2003

(65) Prior Publication Data

US 2005/0131228 A1 Jun. 16, 2005

(30) Foreign Application Priority Data

Nov. 16, 2001 (AT) .............................. A 1807/2001
Jun. 25, 2002 (DE) ................................ 102 29 100

(51) Int. Cl.
C07D 251/60 (2006.01)
C07D 251/62 (2006.01)

(52) U.S. Cl. .................................. 544/203; 544/201

(58) Field of Classification Search ............... 544/201, 544/203
See application file for complete search history.

(56) References Cited

U.S. PATENT DOCUMENTS

| | | | |
|---|---|---|---|
| 2,647,119 A | 7/1953 | Haworth et al. | |
| 2,863,869 A | 12/1958 | Elmer et al. | |
| 3,132,143 A | 5/1964 | Fogagnolo et al. | |
| 3,207,744 A | 9/1965 | O'Hara et al. | |
| 3,321,477 A | 5/1967 | Hyman et al. | |
| 3,325,493 A | 6/1967 | Shimamura et al. | |
| 3,454,571 A | 7/1969 | Kokubo et al. | |
| 3,637,686 A | 1/1972 | Kokubo et al. | |
| 6,380,385 B1 | 4/2002 | Canzi et al. | |
| 6,774,234 B1* | 8/2004 | Noe' | 544/203 |
| 6,790,956 B1 | 9/2004 | Coufal | |

FOREIGN PATENT DOCUMENTS

| | | |
|---|---|---|
| AT | 404 018 B | 7/1998 |
| GB | 1148767 | 4/1969 |
| WO | WO 96/23778 | 8/1996 |
| WO | WO 97/20826 | 6/1997 |
| WO | WO 00/29393 | 5/2000 |
| WO | WO 00/29393 A1 | 5/2000 |
| WO | WO 01/36397 A1 | 5/2001 |
| WO | WO 200136397 A1 * | 5/2001 |
| WO | WO 01/46159 A2 | 6/2001 |
| WO | WO 01/46159 A2 * | 6/2001 |
| WO | WO 02/100839 A1 | 12/2002 |

OTHER PUBLICATIONS

International Search Report of PCT/DE02/04251, dated Apr. 22, 2003.
International Preliminary Examination Report of PCT/DE02/04251, dated Apr. 6, 2004.
English translation of International Preliminary Examination Report, International Application No. PCT/DE2002/004251; International Filing Date Nov. 14, 2002; dated Apr. 6, 2004.
George M. Crews, et al.; *Melamine and Guanamines*, 2005 Wiley-VCH Verlag GmbH & Co. KGaA, Weinheim, pp. 1-17.

* cited by examiner

*Primary Examiner*—Venkataraman Balasubramanian
(74) *Attorney, Agent, or Firm*—Christie, Parker & Hale, LLP

(57) ABSTRACT

The invention relates to a method for producing melem-free melamine by means of aqueous processing of a melted mass of melamine which is obtained using a high-pressure method. According to the inventive method, the melted mass of melamine is quenched by means of an aqueous solution containing alkalis, following the isolation of the off-gases, and is directly transferred into an aqueous alkaline melamine solution, out of which the melamine is then crystallized. The invention thus enables melamine to be obtained, with a melam content of less than 1000 ppm and a melem content of less than 50 ppm. The invention also relates to a quenching agent.

12 Claims, 1 Drawing Sheet

METHOD FOR PRODUCING MELEM-FREE MELAMINE AND QUENCHING AGENTS

CROSS-REFERENCE TO RELATED APPLICATION(S)

This application is a National Phase Patent Application of International Application Number PCT/DE02/04251, filed on Nov. 14, 2002, which claims priority of Austrian Patent Application Number A 1807/2001, filed on Nov. 16, 2001, and German Patent Application Number 102 29 100.4, filed on Jun. 25, 2002.

FIELD OF THE INVENTION

The application relates to a process for preparing melem-free melamine by direct conversion of a melamine melt obtained from a high-pressure process into an aqueous alkaline melamine solution by quenching with aqueous alkali-containing solution and then crystallizing the melamine. The invention also relates to quenchers having the features of claims 9 and 10.

BACKGROUND OF THE INVENTION

In the high-pressure processes for preparing melamine, generally, urea melt and if appropriate gaseous ammonia, in the absence of a catalyst at temperatures, for instance, between 325 and 450° C., preferably between 350 and 425° C. and pressures between 50 and 250 bar, are concentrated into liquid melamine and off-gas principally consisting of ammonia and carbon dioxide, with small amounts of gaseous melamine. This reaction mixture is then worked up, depending on the process in various ways, at high pressure and at high temperature. This is followed by melamine solidification, which can be carried out in two ways: in the dry processes, the melamine melt is solidified in the absence of water, with or without ammonia, with simultaneous expansion, cooled and then isolated. However, the disadvantage of these dry processes is that during the expansion many by-products are formed, for example melam and melem, which interfere in the later melamine processing steps, especially in processing to form melamine resins and their secondary products. The condensation by-product melem is particularly interfering.

In a combined dry/wet process according to U.S. Pat. No. 3,637,686, the melamine melt is first solidified with ammonia in the absence of water and the solid melamine is then worked up in aqueous ammoniacal solution to remove the by-products present in the melamine and formed in part during the solidification. However, in such a recrystallization step, the melamine hydrolysis which takes place in parallel to by-product breakdown can mean a considerable loss of yield.

Another possible method for solidifying melamine from a high-pressure process is described in U.S. Pat. No. 3,132,143 or WO 01/36397. There, the reaction mixture obtained directly from the melamine reactor is expanded into a quencher and, in the presence of aqueous ammonia and carbon dioxide, is transferred to a carbon dioxide- and by-product-containing melamine solution. The disadvantage of the process described is that in the hydrolytic by-product breakdown in the presence of carbon dioxide, owing to the relatively low pH, very high temperatures and long residence times are required in order to achieve the desired degree of breakdown of the by-products.

Another possible method for solidifying the melamine melt from a high-pressure process is described in WO 00/29393. There, the melamine melt, using an aqueous ammoniacal solution, is converted to a melamine suspension and the melamine is isolated therefrom. The disadvantage of this process is that, as in the dry processes, during the solidification step, by-products are additionally formed which can be removed from the melamine suspension only by very long residence times in the aqueous phase, which means high melamine loss due to hydrolysis. Furthermore, in the suspension procedure, the risk of deposits and blockages due to by-products crystallizing out is disadvantageous.

SUMMARY OF THE INVENTION

The object was therefore to find a process by which it is possible, with the highest possible yield of melamine, to achieve a melem content of less than 50 ppm. Unexpectedly, the object was achieved by means of the fact that the melamine melt coming from a high-pressure process, after separating off the off-gases, is converted into an aqueous alkaline melamine solution by quenching with aqueous alkali-containing solution and the melamine is then crystallized out.

The present invention therefore relates to a process for preparing melem-free melamine by aqueous work-up of a melamine melt obtained from a high-pressure process, which is characterized in that the melamine melt, after separating off the off-gases, is quenched with an aqueous alkali-containing solution, converted in the process into an aqueous alkaline melamine solution and then solid melamine is obtained by subsequent crystallization.

By direct conversion of the melamine melt into a melamine solution it is possible, firstly, to transfer the melamine quality formed in the high-pressure part of the melamine plant, without additional by-product formation, into the aqueous work-up part. Secondly, it is possible, by using an alkali-containing solution for quenching the melamine melt, to break down the by-products introduced into the aqueous work-up part with the melamine melt as early as in the quencher, as a result of which the entire residence time of the melamine in the aqueous work-up part and thus the melamine loss owing to hydrolysis may be minimized.

DETAILED DESCRIPTION

Figure 1:
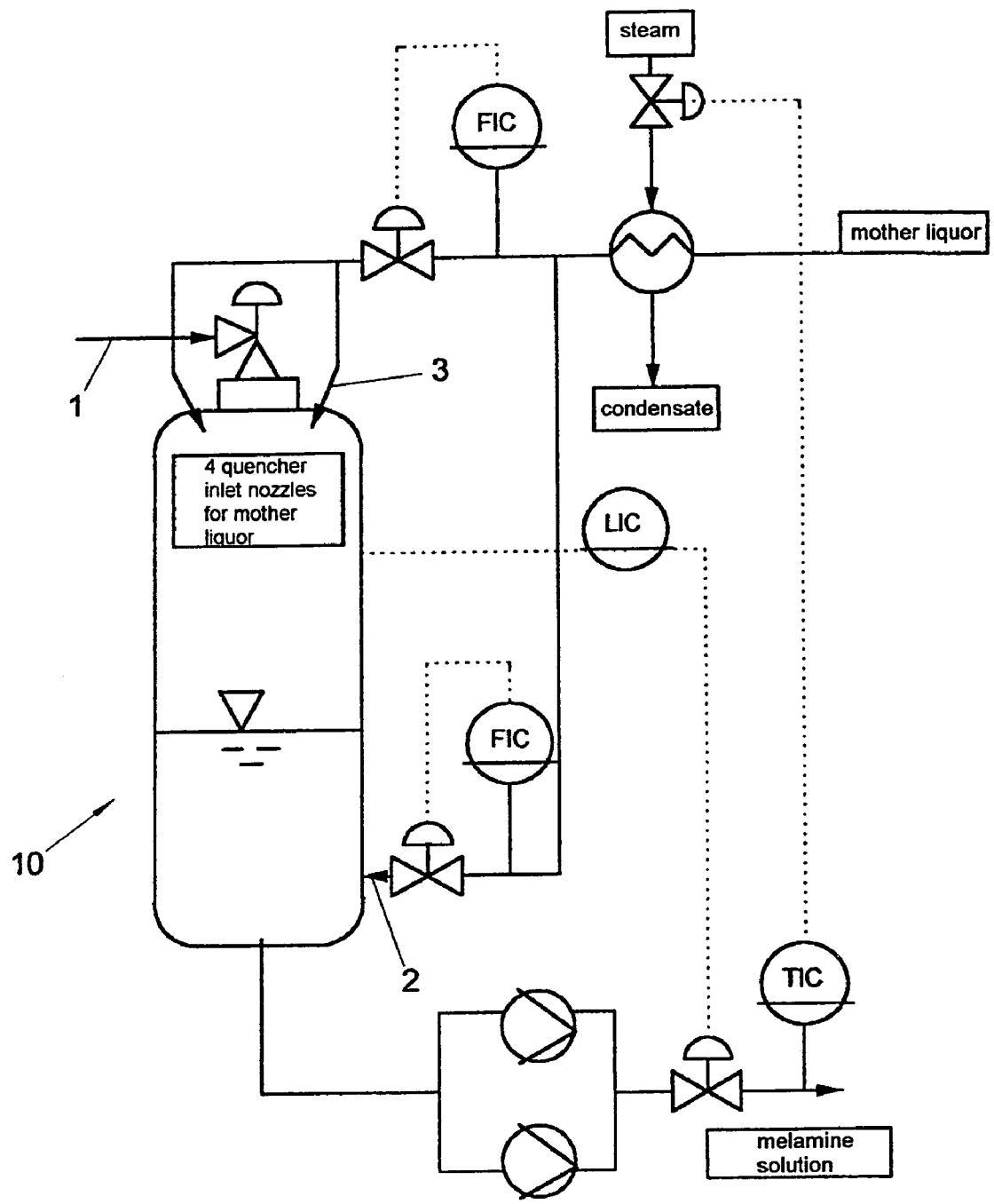
FIG. 1 shows a quencher 10 which is used for the inventive process.

The melamine melt to be worked up by the present process originates from a high-pressure process and is passed to the quencher at a temperature of about 330 to 400° C., preferably from about 330 to 380° C., particularly preferably from about 330 to 360° C. and at a pressure from about 50 to 600 bar, preferably from about 50 to 250 bar, particularly preferably from about 70 to 170 bar.

In the melamine melt from a high-pressure process, two types of by-products are present. The oxygen-containing by-products in the melamine melt include, for example, carbon dioxide, ammeline, ammelide, ureidomelamine or unreacted urea. Condensation by-products is a term applied, for example, to melem or melam.

In the present process, any melamine melt originating from a high-pressure process can be used after separating off the reaction off-gases. Particularly pure melamine can be obtained by the present process if the melamine melt is prepurified in the high-pressure part of the melamine plant.

It is particularly advantageous here to substantially remove the oxygen-containing by-products, for example by treating the melamine melt with gaseous ammonia, and to remove the condensation by-products in part, for example by cooling and/or holding the melamine melt at high ammonia pressure, from the melamine melt. Furthermore, it is particularly advantageous to use ammonia-saturated melamine melt in the present process.

The melamine melt is preferably introduced into the quencher by spraying in the melamine melt in order to achieve fine distribution of the same. At the same time as the melamine melt, an aqueous alkali-containing solution is introduced into the quencher, preferably in spray-cone form. The spray apparatuses are preferably disposed in such a way that the contact between melamine melt and aqueous alkali-containing solution takes place immediately after the melamine melt has entered the apparatus. For example, the melamine melt enters centrally in the upper apparatus part, while the aqueous alkali-containing solution is sprayed into the quencher from the top via one or more nozzles. Another possible method of introducing the melamine melt and the aqueous alkali-containing solution is to use a two-component nozzle. In this manner the melamine melt is converted directly into the dissolved form on contact with the solution sprayed in. It is also possible to divide the total amount of aqueous alkali-containing solution introduced for quenching the melamine melt into two or more subquantities, for example to divide it in a ratio of about 1:1 to 1.5:1, of which one subquantity is introduced into the apparatus from the top, while the second subquantity is introduced, for improved mixing, laterally in the lower apparatus part.

The amount of the aqueous alkali-containing solution introduced into the quencher is, for example, such that the aqueous alkaline melamine solution discharged from the quencher has a concentration of about 5 to 10% by weight, preferably from about 6 to 9% by weight of melamine.

The temperature of the aqueous alkali-containing solution introduced into the quencher is selected so that the quenching of the melamine melt takes place at a temperature of from 100 to 150° C., preferably from about 110 to 145° C., particularly preferably from about 120 to 140° C. The pressure during quenching is from 1 to 7 bar, preferably from 2 to 6 bar, particularly preferably from 3 to 5 bar.

The alkali content of the aqueous alkali-containing solution fed into the quencher is from about 0.05 to 0.5% by weight, preferably from about 0.05 to 0.3% by weight. The alkaline constituent of the solution which can be used is, for example, sodium hydroxide, potassium hydroxide or ammonia; preferably sodium hydroxide is used. Preferably, the alkaline constituent in the aqueous alkali-containing solution used for quenching principally originates from the mother liquor of the melamine crystallization.

The solution used for quenching therefore preferably comprises a recirculated part of the crystallization mother liquors, and in addition the condensed weak ammonia-containing vapours of the melamine crystallization may be present, and in addition fresh condensate is present in the solution used for quenching.

The mode of operation of the quencher according to the present invention offers a plurality of advantages which are explained below.

By means of the direct conversion of the melamine melt into a melamine solution in the quencher it is possible to ensure the transition from the melt phase to the aqueous work-up of the melamine plant without quality impairment owing to by-product formation. This means that in the aqueous work-up part only the by-products already introduced with the melamine melt need to be broken down, but in contrast to the pure dry processes or the processes which operate in suspension, no by-products are additionally formed during expansion.

The residence time in the aqueous work-up part is defined by the by-product content present in the quencher, that is to say the lower the by-product content the shorter the residence time which can be selected in order to achieve the particular low by-product concentration required in the end product.

A residence time as short as possible is desirable in order to keep the melamine hydrolysis which occurs at the same time as the by-product breakdown as low as possible.

In order to be able to break down by hydrolysis the by-products which are introduced into the aqueous work-up together with the melamine, the by-products must be present in dissolved form. Since the by-products melam and melem are less soluble than melamine, these are for the most part present in solid form in the quencher in the suspension procedure, whereas the more readily soluble melamine, even in the suspension procedure, is present in dissolved form in the solution which is in equilibrium with the suspension. This means that in the case of the suspension procedure in the quencher, although the unwanted melamine hydrolysis takes place, the by-product breakdown which is wanted can, however, not take place.

In contrast thereto, in a process corresponding to the present invention, the hydrolytic by-product breakdown can begin as early as in the quencher, since all of the by-products present in the melamine are in solution as early as in the quencher.

The hydrolytic breakdown of by-products proceeds more rapidly, the higher the pH in the solution. If the by-product breakdown is carried out at low pHs, it is necessary to carry out the reaction at correspondingly high temperatures, generally at temperatures above 150° C., and with long residence times. However, owing to the melamine hydrolysis which proceeds at the same time, this is not desirable. As a result of the free sodium hydroxide solution present in the quencher in accordance with the present invention, and the resultant high pH of about pH 9 to pH 12, it is possible to keep the temperature low during the by-product breakdown and nevertheless achieve a sufficiently rapid reaction.

The melamine solution obtained in the quencher is, if appropriate after reacting with concentrated aqueous alkali-containing solution, allowed to stand. The residence time is about 5 to 60 min, preferably about 20 to 40 min. The resultant aqueous alkaline melamine solution is, if appropriate after removing ammonia, dilution, treatment with activated carbon and adjusting the pH, fed to a crystallization unit, where, for example by temperature reduction and/or applying a vacuum, the melamine is crystallized out. The melamine is then filtered, dried and isolated.

By means of the present process it is possible to prepare melamine having a melam content of <1 000 ppm and a melem content of <50 ppm, which can be fed to any desired further processing.

The alkaline mother liquor taken off in the crystallizer can, if appropriate after mixing with the filtrate of the melamine filtration, be divided into two substreams in a ratio of from about 2.5:1 to 3.0:1. The first substream is recirculated to the aqueous melamine work-up. It is possible here to use a portion or all of the recirculated mother liquor for quenching the melamine melt. The second substream of crystallizer mother liquor and filtrate is ejected and fed to wastewater treatment.

EXAMPLE 1

Melamine melt from a high-pressure melamine plant was sprayed at a temperature of 360° C. and a pressure of 245 bar into a quencher which was operated at a pressure of 2.5 bar. The melamine melt had a starting concentration of 11 850 ppm of melam and 670 ppm of melem, was substantially free from oxygen-containing impurities and was virtually ammonia-saturated. At the same time as the melamine melt, an aqueous solution having an NaOH content of 0.3% by weight was introduced into the quencher. The ratios of melamine melt and aqueous NaOH solution were chosen so that in the quencher a 5% strength solution of melamine and by-products was present. The temperature of the melamine solution in the quencher was 130° C. After a residence time of 30 min under these temperature and pressure conditions, the solution was cooled, the resultant melamine suspension was neutralized and dried and the melamine was analysed. The melam content in the melamine was 810 ppm, and the melem content <50 ppm.

EXAMPLE 2

The experimental procedure was similar to that of Example 1. The melamine melt introduced into the quencher was substantially free from oxygen-containing by-products, but the condensation by-products melam and melem had not been removed by prepurification in the high-pressure part. Thus the starting content of melam in the melamine melt was 35 000 ppm, and that of melem was 5 600 ppm. The melamine melt was introduced at 380° C. and 70 bar into the quencher which was operated at 2.5 bar. At the same time as the melamine melt, an aqueous solution having an NaOH content of 0.2% by weight was introduced into the quencher. The ratios of melamine melt and aqueous NaOH solution were chosen so that an 8% solution of melamine by-products was present in the quencher. The temperature of the melamine solution in the quencher was 130° C. After a residence time of 60 min in the quencher, the solution was cooled, the resultant melamine suspension was neutralized and dried and the melamine was analysed. The melam content in the melamine was 2 700 ppm, and the melem content 100 ppm.

Referring to FIG. 1, the top of the quencher 10 is disposed a melamine melt intake 1, with there being disposed laterally thereto four quencher inlet nozzles for hot mother liquor (aqueous alkali-containing solution). The hot mother liquor at approximately 120° C. mixes with the melamine melt at approximately 350° C., so that in the upper region of the quencher a mixture temperature of approximately 140° C. is established. This mother liquor/melamine mixture is then again mixed with cool mother liquor at approximately 120° C., so that at the bottom of the quencher 10 a temperature of approximately 130° C. is established. The feed 2 into the lower region is performed tangentially to the wall of the vessel.

This has the advantage that a higher temperature is achieved in the upper region of the apparatus, and, by admixing a colder mother liquor stream, a cooling is deliberately achieved in the lower region of the apparatus.

As a result of the higher temperature in the upper region of the quencher, at the top a higher pressure is also established compared to the lower region of the apparatus (=saturated vapour pressure in accordance with the temperature). By admixing cooler liquid in the lower region, the pressure also decreases.

This is beneficial, since as a result the NPSH value (pressure-holding height) of the bottom take-off pump increases, as a result of which the risk of pump cavitation decreases.

Improved mixing is achieved by means of the fact that the lower mother liquor stream flows in tangentially.

At the top of the quencher are situated the four spray nozzles for the mother liquor. Each of the nozzles is designed for a defined flow rate to be processed. The nozzles only operate optimally (with respect to spray geometry and risk of blockage) at this flow rate.

An advantage achieved by the feed divided into two with respect to the optimum operating point of the nozzles is that even under partial load of the melamine plant, that is to say feed of <100% of the amount of melamine melt into the quencher, the mother liquor spray nozzles can always be charged with the same (that is to say optimum) flow rate, by, for example, setting the lower mother liquor feed to "zero".

As a result, even under partial load of the melamine plant, an optimum distribution/optimum nozzle spray pattern of the mother liquor in the quencher is always achieved.

The invention claimed is:

1. A process for preparing solid melem-free melamine by aqueous work-up of a melamine melt obtained from a high-pressure process, characterized in that the melamine melt is provided at a temperature between 330 and 400° C. and a pressure between 50 and 600 bar, the process comprising:
   separating the off-gases from the melamine melt;
   treating the melamine melt with gaseous ammonia to produce an ammonia-saturated melamine melt;
   quenching the ammonia-saturated melamine melt with an aqueous alkali-containing solution after the off-gases have been separated, thereby producing an aqueous alkaline melamine solution; and
   crystallizing solid melamine from the aqueous alkaline melamine solution.

2. The process according to claim 1, characterized in that the aqueous alkali-containing solution is an aqueous solution of NaOH.

3. The process according to claim 1 or 2, characterized in that the aqueous alkali-containing solution comprises a mother liquor recirculated from the melamine crystallization.

4. The process according to claim 1, characterized in that the oxygen-containing by-products have been substantially removed, and the condensation by-products removed in part, from the melamine melt before quenching.

5. The process according to claim 1, characterized in that the melamine melt is quenched with aqueous alkali-containing solution at a temperature of from 100 to 150° C.

6. The process according to claim 1, characterized in that the melamine melt is quenched with aqueous alkali-containing solution at a pressure of from 1 to 7 bar.

7. The process according to claim 1, characterized in that the concentration of alkali in the aqueous alkali-containing solution is between 0.05 and 0.5% by weight.

8. The process according to claim 1, characterized in that the aqueous alkaline melamine solution, after addition of concentrated aqueous alkali-containing solution, is allowed to stand for from 5 to 60 mm.

9. The process according to claim 1, wherein the aqueous alkali-containing solution quenches the melamine melt through at least one inflow orifice orientated tangentially to the wall of a quencher.

10. The process according to claim 9, characterized in that the aqueous alkali-containing solution quenches the melamine melt through two spatially separated inflow orifices.

11. The process according to claim 9 characterized in that at least one inflow orifice is disposed in the region of the feed of the hot melamine melt.

12. The process according to claim 10 or 11, characterized in that at least one inflow orifice is disposed in the region of a feed of cool mother liquor.

* * * * *

UNITED STATES PATENT AND TRADEMARK OFFICE
CERTIFICATE OF CORRECTION

PATENT NO. : 7,176,309 B2
APPLICATION NO. : 10/495619
DATED : February 13, 2007
INVENTOR(S) : Schröder et al.

It is certified that error appears in the above-identified patent and that said Letters Patent is hereby corrected as shown below:

On the Title Page

(54) Title      Delete "METHOD FOR PRODUCING MELEM-FREE MELAMINE AND QUENCHING AGENTS",
Insert --PROCESS FOR PREPARING MELEM-FREE MELAMINE AND QUENCHERS--

In the Claims

Column 6, line 65, Claim 8      Delete "mm",
Insert --min--

Signed and Sealed this

Eleventh Day of March, 2008

JON W. DUDAS
*Director of the United States Patent and Trademark Office*

UNITED STATES PATENT AND TRADEMARK OFFICE
CERTIFICATE OF CORRECTION

PATENT NO. : 7,176,309 B2
APPLICATION NO. : 10/495619
DATED : February 13, 2007
INVENTOR(S) : Schröder et al.

It is certified that error appears in the above-identified patent and that said Letters Patent is hereby corrected as shown below:

On the Title Page

(54) Title and Column 1 lines 1 and 2

Delete "METHOD FOR PRODUCING MELEM-FREE MELAMINE AND QUENCHING AGENTS",
Insert --PROCESS FOR PREPARING MELEM-FREE MELAMINE AND QUENCHERS--

In the Claims

Column 6, line 65, Claim 8

Delete "mm",
Insert --min--

This certificate supersedes the Certificate of Correction issued March 11, 2008.

Signed and Sealed this

First Day of April, 2008

JON W. DUDAS
*Director of the United States Patent and Trademark Office*